US011091168B2

(12) United States Patent
Chou et al.

(10) Patent No.: US 11,091,168 B2
(45) Date of Patent: Aug. 17, 2021

(54) AUTONOMOUS DRIVING SUPPORT SYSTEMS INCLUDING VEHICLE HEADREST MONITORING DEVICES AND METHODS INCORPORATING THE SAME

(71) Applicant: Toyota Motor Engineering & Manufacturing North America, Inc., Plano, TX (US)

(72) Inventors: Chungchih Chou, Ann Arbor, MI (US); Paul Schmalenberg, Ann Arbor, MI (US); Muhamed Kusay Farooq, Dearborn, MI (US)

(73) Assignee: TOYOTA MOTOR ENGINEERING & MANUFACTURING NORTH AMERICA, INC., Plano, TX (US)

( * ) Notice: Subject to any disclaimer, the term of this patent is extended or adjusted under 35 U.S.C. 154(b) by 283 days.

(21) Appl. No.: 16/264,414

(22) Filed: Jan. 31, 2019

(65) Prior Publication Data

US 2020/0247425 A1 Aug. 6, 2020

(51) Int. Cl.
*B60W 50/00* (2006.01)
*A61B 5/0478* (2006.01)
(Continued)

(52) U.S. Cl.
CPC ........... *B60W 50/0098* (2013.01); *A61B 5/05* (2013.01); *A61B 5/163* (2017.08); *A61B 5/165* (2013.01);
(Continued)

(58) Field of Classification Search
CPC ..... B60W 50/00; B60W 50/0098; A61B 5/00; A61B 5/0478; A61B 5/04; G06F 3/16;
(Continued)

(56) References Cited

U.S. PATENT DOCUMENTS 4,516,116 A * 5/1985 White .................. B66C 23/905
340/665
4,611,199 A * 9/1986 Seko ........................ A61B 5/18
180/272
(Continued)

FOREIGN PATENT DOCUMENTS

JP 2011133548 A * 7/2011 ............. G02B 27/01
JP 2011133548 A 7/2011
(Continued)

OTHER PUBLICATIONS

Borghino, Dario,"Tiny new sensor could simplify brain wave research", Jun. 6, 2012 https://newatlas.com/author/dario-borghino/.
(Continued)

*Primary Examiner* — Yuri Kan
(74) *Attorney, Agent, or Firm* — Dinsmore & Shohl LLP

(57) ABSTRACT

A driver support system of a vehicle that includes a neuroimaging sensor and a positioning sensor, the neuroimaging sensor detects neurological signals of an occupant and the positioning sensor detects a position of the occupant. The neuroimaging sensor is configured to be positioned within the vehicle distally from the occupant. The system further includes a processor and non-transitory computer-readable medium storing computer-readable instructions executed by the processor to generate a brainwave map based on the neurological signals, calibrate the brainwave map based on the position of the occupant, and determine a mental state of the occupant based on the calibrated-brainwave map. The processor further actuates vehicle support control in response to determining the mental state of the occupant.

20 Claims, 8 Drawing Sheets

(51) Int. Cl.

| | | |
|---|---|---|
| *G09G 5/00* | (2006.01) | |
| *G02B 27/01* | (2006.01) | |
| *B60Q 1/00* | (2006.01) | |
| *B60W 50/14* | (2020.01) | |
| *B60W 10/18* | (2012.01) | |
| *B60W 10/20* | (2006.01) | |
| *B60W 10/30* | (2006.01) | |
| *A61B 5/18* | (2006.01) | |
| *A61B 5/05* | (2021.01) | |
| *A61B 5/16* | (2006.01) | |
| *B60W 30/18* | (2012.01) | |

(52) U.S. Cl.
CPC ............... *A61B 5/18* (2013.01); *B60W 10/18* (2013.01); *B60W 10/20* (2013.01); *B60W 10/30* (2013.01); *B60W 30/18* (2013.01); *B60W 50/14* (2013.01); *A61B 2560/0223* (2013.01); *B60W 2050/143* (2013.01); *B60W 2420/42* (2013.01); *B60W 2420/50* (2013.01); *B60W 2422/00* (2013.01); *B60W 2540/043* (2020.02); *B60W 2540/22* (2013.01); *B60W 2540/26* (2013.01); *B60W 2710/18* (2013.01); *B60W 2710/20* (2013.01); *B60W 2710/30* (2013.01); *B60W 2720/106* (2013.01)

(58) Field of Classification Search
CPC .. B60Q 1/00; G02B 27/01; B60R 1/00; A61F 2/72; G08B 21/00; G09G 5/00
See application file for complete search history.

(56) References Cited

U.S. PATENT DOCUMENTS

| | | | |
|---|---|---|---|
| 5,036,858 A | 8/1991 | Carter et al. | |
| 5,801,667 A * | 9/1998 | Shimizu | H04N 7/183 340/435 |
| 6,587,713 B1 * | 7/2003 | Freeman | A61F 4/00 600/300 |
| 7,876,203 B2 * | 1/2011 | Traylor | G08G 1/165 340/435 |
| 8,676,273 B1 * | 3/2014 | Fujisaki | H04M 1/0202 455/567 |
| 8,866,622 B2 | 10/2014 | Lee et al. | |
| 9,639,804 B1 | 5/2017 | Palmer et al. | |
| 9,809,169 B1 | 11/2017 | Naboulsi | |
| 2008/0269629 A1 | 10/2008 | Reiner | |
| 2009/0112281 A1 * | 4/2009 | Miyazawa | A61N 1/36071 607/46 |
| 2010/0010365 A1 | 1/2010 | Terao et al. | |
| 2013/0093579 A1 * | 4/2013 | Arnon | B60Q 9/008 340/425.5 |
| 2014/0277582 A1 * | 9/2014 | Leuthardt | A61F 2/54 623/25 |
| 2015/0002373 A1 * | 1/2015 | Kobayashi | A61B 5/02416 345/8 |
| 2015/0009100 A1 * | 1/2015 | Haneda | B60R 1/00 345/7 |
| 2015/0351655 A1 * | 12/2015 | Coleman | A61B 5/0482 600/301 |
| 2016/0103322 A1 * | 4/2016 | Hall, Jr. | G02B 27/0172 29/428 |
| 2016/0320840 A1 | 11/2016 | Hwang et al. | |
| 2017/0042439 A1 * | 2/2017 | Yeow | A61B 5/0478 |
| 2017/0140232 A1 | 5/2017 | Banno et al. | |
| 2017/0305349 A1 * | 10/2017 | Naboulsi | B60R 1/025 |
| 2017/0311831 A1 * | 11/2017 | Freer | A61B 5/11 |
| 2018/0085000 A1 * | 3/2018 | Weffers-Albu | A61B 5/7246 |
| 2019/0171409 A1 * | 6/2019 | Boulanger | G06F 16/638 |

FOREIGN PATENT DOCUMENTS

| | | |
|---|---|---|
| KR | 101338041 B1 | 12/2013 |
| WO | 9715033 A2 | 4/1997 |
| WO | 2002000095 A2 | 1/2002 |
| WO | 2014001928 A2 | 1/2014 |
| WO | 2014083375 A1 | 6/2014 |
| WO | 2016035268 A1 | 3/2016 |
| WO | 2016097937 A1 | 6/2016 |

OTHER PUBLICATIONS

Bennakhi, Ahmad, "Homonoia: when your car reads your mind", 2017 https://www.sciencedirect.com/science/article/pii/S1877050917313133.

* cited by examiner

AUTONOMOUS DRIVING SUPPORT SYSTEMS INCLUDING VEHICLE HEADREST MONITORING DEVICES AND METHODS INCORPORATING THE SAME

TECHNICAL FIELD

The present specification generally relates to vehicle systems capable of providing autonomous driving support based on a mental status of an occupant, and in particular, monitoring devices mounted within a vehicle for detecting various emotional states of an occupant of the vehicle for dynamically implementing driving support measures, and methods incorporating the same.

BACKGROUND

Occupants of automotive vehicles may generally experience various emotional states during operation of an automotive vehicle. Such emotional states may be initiated in response to a variety of factors, some of which may be unrelated to and/or unconnected with an active operation of the automotive vehicle. Irrespective of the cause, some emotional states may impair an occupant's ability to operate an automotive vehicle. Further, in some instances an occupant may be unaware of the present impairment caused by the current emotional state, further inhibiting an occupant's ability to effectively operate the vehicle.

Vehicle systems and devices that may inform an occupant of a present impairment may be productive in notifying the occupant of such a condition and minimize an occurrence of ineffective operation of the automotive vehicle. These systems and devices may include, for example, an electroencephalography (EEG) sensor that is capable of monitoring an occupant's brain activity to determine whether the occupant is actively focused on operating the automotive vehicle, watching a roadway ahead of the vehicle, and/or the like. However, such systems and devices generally require an occupant of the automotive vehicle to wear an apparatus containing the EEG sensor or be in constant, physical contact with a portion of the vehicle that includes the EEG sensor mounted thereon while operating the vehicle.

Requiring an occupant of the automotive vehicle to maintain physical contact with the monitoring system and/or device may inhibit the occupant's comfort while operating the vehicle, impair the occupant's operation of the vehicle, and/or be ineffective in continuously monitoring an occupant's mental activity throughout a travel period. Furthermore, such systems and/or devices may generally only provide a communicative message, in the form of an alert, upon detecting an impaired-condition of the occupant.

Accordingly, a need exists for non-invasive vehicle systems that actively monitor an occupant's mental state without requiring the occupant to maintain direct contact with said system or device. Further, vehicle systems that provide driving support responses upon determining an impairment of an occupant pursuant to the detected-mental state may be further beneficial.

SUMMARY

In one embodiment, a driver support system of a vehicle comprises a neuroimaging sensor that detects neurological signals of an occupant of the vehicle. The neuroimaging sensor is configured to be positioned within the vehicle distally from the occupant such that the neuroimaging sensor is adjacent to the occupant. The system further comprises a positioning sensor that detects a position of the occupant relative to the neuroimaging sensor, a processor and non-transitory computer-readable medium storing computer-readable instructions that, when executed, causes the processor to generate a brainwave map of the occupant based on the neurological signals detected by the neuroimaging sensor. The processor further calibrates the brainwave map based on the position of the occupant relative to the neuroimaging sensor, determines a mental state of the occupant based on the calibrated-brainwave map, and actuates vehicle support control in response to determining the mental state of the occupant.

In another embodiment, a vehicle comprises a seat for supporting an occupant received thereon and a driver support system including at least one neuroimaging sensor and at least one positioning sensor. The neuroimaging sensor detects neurological signals of the occupant and the positioning sensor detects a position of the occupant relative to the neuroimaging sensor. The neuroimaging sensor is configured to be positioned along the seat and adjacent to the occupant received thereon. The driver support system further comprises a processor and non-transitory computer-readable medium storing computer-readable instructions thereon that, when executed, causes the processor to generate a brainwave map of the occupant based on the neurological signals detected by the neuroimaging sensor. The processor further calibrates the brainwave map based on the position of the occupant relative to the neuroimaging sensor, determines an emotional state of the occupant based on the calibrated-brainwave map, and initiates control of a vehicle system in response to determining the emotional state of the occupant.

In another embodiment, a method of autonomously supporting driver control of a vehicle comprises generating a visual indicator along a surface of the vehicle at a predetermined frequency and detecting a neurological signal of an occupant by a neuroimaging sensor positioned within the vehicle proximate to the occupant. The method further comprises determining whether the occupant identified the visual indicator based on the neurological signal detected by the neuroimaging sensor and controlling a driver support system in response to determining that the occupant identified the visual indicator.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Embodiments of the present disclosure are generally directed to driver support systems that may provide vehicle support control for an occupant of the vehicle, and in particular, initiate autonomous or semiautonomous operation of one or more vehicle systems dependent on a determined mental and/or emotional state of the occupant. Vehicle systems that may be controlled by the driver support system of the present disclosure may include, for example, vehicle steering, vehicle braking, and vehicle acceleration. Additionally or alternatively, the vehicle system controlled by the driver support system of the present disclosure may further include a technology or device of the vehicle, such as, for example, an HVAC device, an audio system, a visual interface or heads-up display, and the like. The mental and/or emotional state of the occupant may be determined by the driver support system via one or more sensors located within a passenger cabin of the vehicle and positioned proximate to the occupant without requiring direct contact between the occupant and the one or more sensors.

One non-limiting example of a driver support system of a vehicle includes a neuroimaging sensor that detects neurological signals of an occupant of the vehicle and a positioning sensor that detects a position of the occupant relative to the neuroimaging sensor. The neuroimaging sensor is configured to be positioned within the vehicle distally from the occupant such that the neuroimaging sensor is adjacent to the occupant. For instance, the neuroimaging sensor may be positioned within a seat of the vehicle, and in particular, positioned within a headrest of the seat. The driver support system further includes a processor and non-transitory computer-readable medium storing computer-readable instructions that, when executed, causes the processor to generate a brainwave map of the occupant based on the neurological signals detected by the neuroimaging sensor. The non-transitory computer-readable medium storing computer-readable instructions further causes the processor to, when executed, calibrate the brainwave map based on the position of the occupant relative to the neuroimaging sensor, determine a mental state of the occupant based on the calibrated-brainwave map, and actuate a vehicle support control measure in response to determining the mental state of the occupant.

Although embodiments herein are described in the context of driver support systems for automotive vehicles, embodiments are not limited thereto. For example, the driver support systems described herein may be configured and compatible for use with various transportation systems, including, for example, motorcycles, bicycles, watercrafts, aircrafts, and/or the like. Other uses should generally be understood and are included within the scope of the present disclosure.

Figure 1:
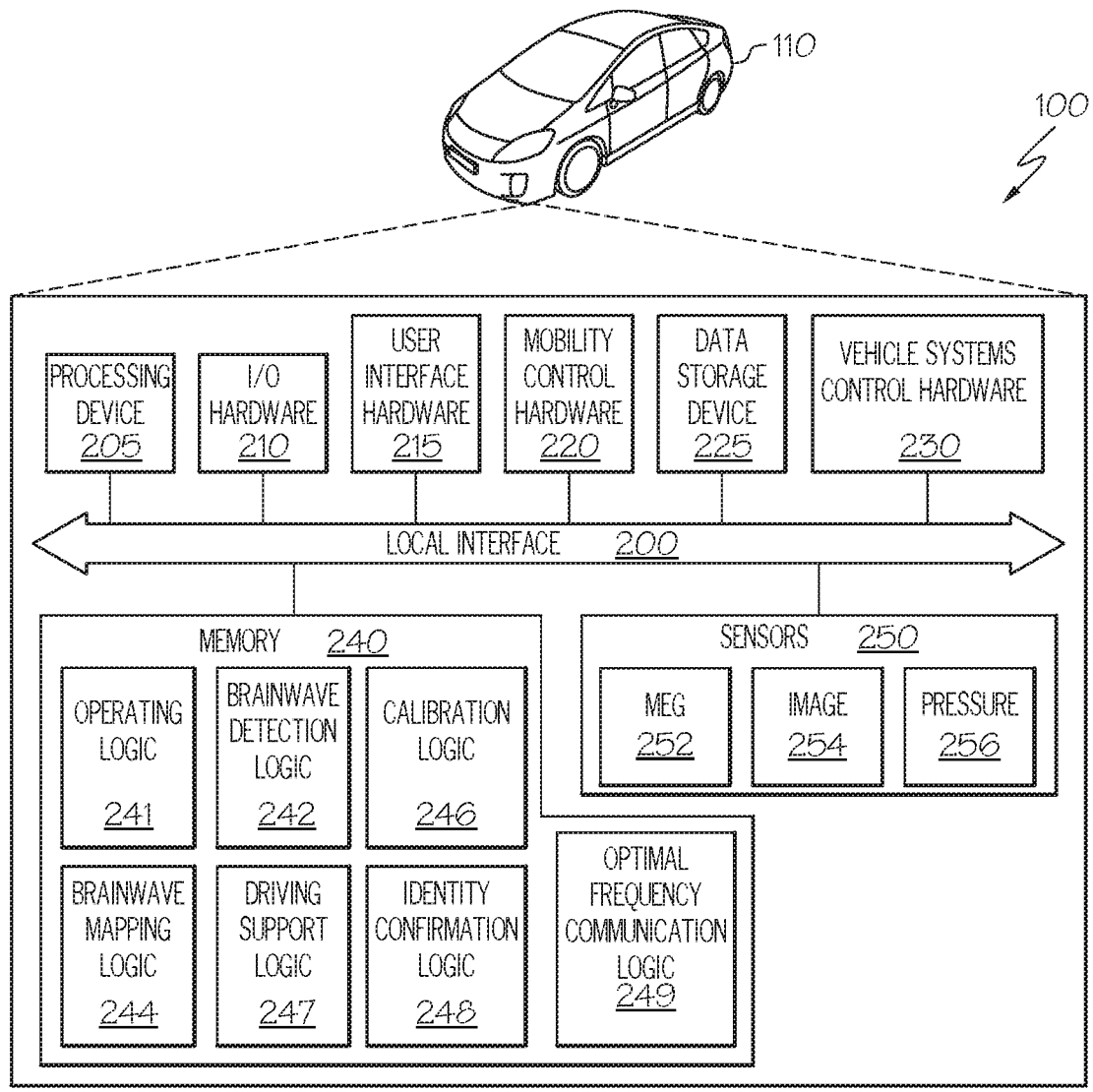
FIG. 1 schematically depicts illustrative hardware components of an illustrative driving support system of a vehicle according to one or more embodiments shown and described herein.

Referring now to the drawings, FIG. 1 schematically depicts a non-limiting example of an illustrative driver support system 100. In particular, FIG. 1 schematically depicts illustrative hardware components of the driver support system 100 that may be used to provide a functionality of the driver support system 100 described in further detail herein. Generally, the illustrative driver support system 100 depicted in FIG. 1 may be positioned within a vehicle 110 and provide particular use in assisting occupants of the vehicle 110 in controlling the vehicle 110 and/or various vehicle systems of the vehicle 110. However, it should be appreciated that the driver support system 100 is not limited to this use and may be used for other purposes without departing from the scope of the present disclosure. For example, the driver support system 100 may be used for other purposes as described in more detail herein, such as uploading a stored-user profile of an occupant seated within the vehicle, identifying potential hazards external to the vehicle 110 for an occupant's awareness, and/or the like.

The example driver support system 100 generally includes a non-transitory computer-readable medium containing one or more programming instructions for completing the various processes described herein, which may be embodied as hardware, software, and/or firmware, according to embodiments shown and described herein. While in some embodiments the various components of the driver support system 100 may be configured as a general purpose computer with the requisite hardware, software, and/or firmware, in other embodiments, the various components of the driver support system 100 may also be configured as a special purpose computer designed specifically for performing the functionality described herein.

Still referring to FIG. 1, the driver support system 100 may include a processing device 205, I/O hardware 210, user interface hardware 215, mobility control hardware 220, a data storage device 225, vehicle systems control hardware 230, a non-transitory memory component 240, and one or more sensors 250. A local interface 200, such as a bus or the like, may interconnect the various components. The processing device 205, such as a computer processing unit (CPU), may be the central processing unit of the driver support system 100, performing calculations and logic operations to execute a program. The processing device 205, alone or in conjunction with the other components, is an illustrative processing device, computing device, processor, or combination thereof. The processing device 205 may include any processing component configured to receive and execute instructions (such as from the data storage device 225 and/or the memory component 240).

The I/O hardware 210 may communicate information between the local interface 200 and one or more other components of the driver support system 100. For example, the I/O hardware 210 may act as an interface between the various components described with respect to FIG. 1 and other components of the driver support system 100 and/or vehicle 110, such as user interface hardware 215 that controls information communicated to an occupant of the vehicle 110, mobility control hardware 220 that control movement and/or steering of the vehicle 110, vehicle systems control hardware 230 that control an operation of various vehicle systems within the vehicle 110, and/or the like. The I/O hardware 210 may be utilized to transmit one or more commands to the other components of the driver support system 100 in some embodiments.

Still referring to FIG. 1, the user interface hardware 215 may include any device, mechanism, system, interactive display, and/or various other hardware components for communicating information from the driver support system 100 to an occupant of the vehicle 110. For example, the user interface hardware 215 may include input hardware, such as a touch screen, button, microphone, and/or other device for receiving inputs from an occupant. The user interface hardware 215 may further include display hardware, such as, for example, a monitor, video card, heads-up display, dashboard display, mirror display, and/or other device for sending or presenting visual data to a user. In some embodiments, a display hardware of the user interface hardware 215 may incorporate audio output hardware that generates and presents audible data to a user, such as, for example, spoken words, tones, music, and/or the like. It should be understood that the user interface hardware 215 may be integrated with the vehicle 110 in various other forms as described in more detail herein.

The mobility control hardware 220 may be one or more hardware components for controlling a movement, power, functionality, or operation of various components of the vehicle 110 that influence a movement and steering of the vehicle 110. For example, the mobility control hardware 220 may include a steering wheel, gas or brake pedal, wheels, and/or the like for controlling a movement, steering, acceleration and/or deceleration of the vehicle 110. Such hardware components may generally be configured to generate and transmit one or more signals to one or more motors coupled to the vehicle 110 to effect movement of the vehicle 110 or the like.

The data storage device 225, which may generally be a storage medium, may contain one or more data repositories for storing data that is received and/or generated. The data storage device 225 may be any physical storage medium, including, but not limited to, a hard disk drive (HDD), solid-state memory, removable storage, and/or the like. While the data storage device 225 is depicted as a local device, it should be understood that the data storage device 225 may be a remote storage device, such as, for example, a server computing device, cloud based storage device, or the like. Illustrative data that may be contained within the data storage device 225 is described below with respect to FIG. 2.

Still referring to FIG. 1, the vehicle systems control hardware 230 may be one or more hardware components for controlling an actuation, functionality, or operation of various vehicle systems included in the vehicle 110. For example, the vehicle systems control hardware 230 may include a heating, ventilation and air conditioning (HVAC) system, a position and/or height of a seat of the vehicle 110, a window of the vehicle 110, and/or the like. The memory component 240 may be configured as a volatile and/or a nonvolatile computer-readable medium and, as such, may include one or more programming instructions thereon that, when executed by the processing device 205, cause the processing device 205 to complete various processes, such as the processes described herein with respect to FIGS. 6, 8 and 10-11. The programming instructions stored on the memory component 240 may be embodied as a plurality of software logic modules, where each logic module provides programming instructions for completing one or more tasks, as described in more detail below with respect to FIGS. 6, 8 and 10-11.

The program instructions contained on the memory component 240 may be embodied as a plurality of software modules, where each module provides programming instructions for completing one or more tasks. For example, FIG. 1 schematically depicts the memory component 240 containing illustrative logic components according to one or more embodiments shown and described herein. The memory component 240 may be configured to store various processing logic, such as, for example, operating logic 241, brainwave detection logic 242, calibration logic 246, brainwave mapping logic 244, driving support logic 247, identity confirmation logic 248, and/or optimal frequency communication logic 249 (each of which may be embodied as a computer program, firmware, or hardware, as an example). The operating logic 241 may include an operating system and/or other software for managing components of the driver support system 100. The brainwave detection logic 242 may include one or more programming instructions for initiating operation of one or more sensors 250 of the driver support system 100 to detect and record brainwave signals (i.e., neural oscillations generated from neural activity in the central nervous system, such as electrical signals transmitted between brain cells) of one or more occupants located within the vehicle 110 and positioned adjacent to the one or more sensors 250.

Still referring to FIG. 1, the brainwave mapping logic 244 may include one or more programming instructions for generating a map of the brainwave signals detected by the one or more sensors 250 and recorded via the brainwave detection logic 242 described above. As described in more detail herein, generating a brainwave map of an occupant of the vehicle 110 may provide data indicative of a mental state and/or emotional condition of an occupant of the vehicle 110 such that the driver support system 100 may initiate a driver support control in response. The calibration logic 246 may include one or more programming instructions for calibrating the brainwave signals detected by the one or more sensors 250 of the driver support system 100 and/or the brainwave map generated by the brainwave mapping logic 244 of the driver support system 100. The calibration logic 246 may initiate one or more sensors 250, and in particular one or more positioning sensors (e.g., imaging sensors 254, pressure sensors 256, and the like), to retrieve data indicative of a position of an occupant relative to the vehicle 110 or the positioning sensor, a head orientation of an occupant relative to the vehicle 110 or the positioning sensor, and/or the like. As described in more detail herein, calibrating a brainwave map generated by the driver support system 100 may enhance an accuracy of the data retrieved by the one or more sensors 250 and of the determination of the mental state and/or emotional condition of an occupant of the vehicle 110, thereby permitting the driver support system 100 to provide a suitable driver support measure in response to a present state of the occupant.

The driving support logic 247 may include one or more programming instructions for controlling and/or influencing the user interface hardware 215, the mobility control hardware 220, the vehicle systems control hardware 230, and/or other devices or components of the vehicle 110 for purposes of facilitating driving support to an occupant of the vehicle 110. As described in more detail herein with respect to FIG. 8, the driving support logic 247 determines a mental state and/or emotional condition of an occupant of the vehicle 110 based on an analysis of the generated brainwave map of the occupant, as computed by the brainwave mapping logic 244, that is determined in accordance with the brainwave signals detected by the one or more sensors 250 and recorded pursuant to the brainwave detection logic 242. Upon determining the mental and/or emotional state of the occupant, the driving support logic 247 may transmit one or more signals to the user interface hardware 215, the mobility control hardware 220, the vehicle systems control hardware 230, and/or other devices or components of the vehicle 110 to initiate some form of control of said hardware in accordance with a present state of the occupant.

Still referring to FIG. 1, the identity confirmation logic 248 may include one or more programming instructions for identifying an identity of an occupant within the vehicle 110, confirming an authorization to operate the vehicle 110, uploading a stored user profile of the occupant including various vehicle system preferences particular to the occupant, and the like. As described in more detail herein with respect to FIG. 9, the identity confirmation logic 248 determines an identity of an occupant of the vehicle 110 by analyzing brainwave signals of the occupant, as detected by the one or more sensors 250 and recorded pursuant to the brainwave detection logic 242. Upon comparing the detected brainwave signals of the occupant to one or more user profiles including stored brainwave signal data for particular occupants, the identity confirmation logic 248 determines whether the detected brainwave signals correspond to a registered user profile. Confirming an identity of an occupant may permit the occupant to proceed with operating the vehicle 110, implementing various system setting preferences associated with the registered user profile, and/or the like.

The optimal frequency communication logic 249 may include one or more programming instructions for generating a visual communication, audible communication, and/or the like to an occupant of the vehicle 110 at a predetermined optimal frequency for purposes of facilitating an effective perception of the communication by the occupant. As described in more detail herein with respect to FIG. 10, the optimal frequency communication logic 249 determines an optimal modulation frequency for a particular occupant positioned within the vehicle 110 based on an analysis of the brainwave signals of the occupant, as detected by the one or more sensors 250 and recorded pursuant to the brainwave detection logic 242. Upon determining the optimal modulation frequency for communicating a message to an occupant, the optimal frequency communication logic 249 may transmit one or more signals to the user interface hardware 215 to initiate a communication at the optimal modulation frequency to effectively enhance a perception and/or recognition of the communication by the occupant. It should be understood that the communication may be in the form of a visual message displayed on a display hardware of the user interface hardware 215 (e.g., a monitor, video card, heads-up display, dashboard display, mirror display, and/or other device for sending or presenting visual data to a user). In other embodiments, the communication may be in the form of an audible message (e.g., spoken words, tones, sounds, music, and the like) transmitted via audio output hardware of the user interface hardware 215 (e.g., a speaker, and/or other device for sending or presenting audible data to a user).

Figure 5:
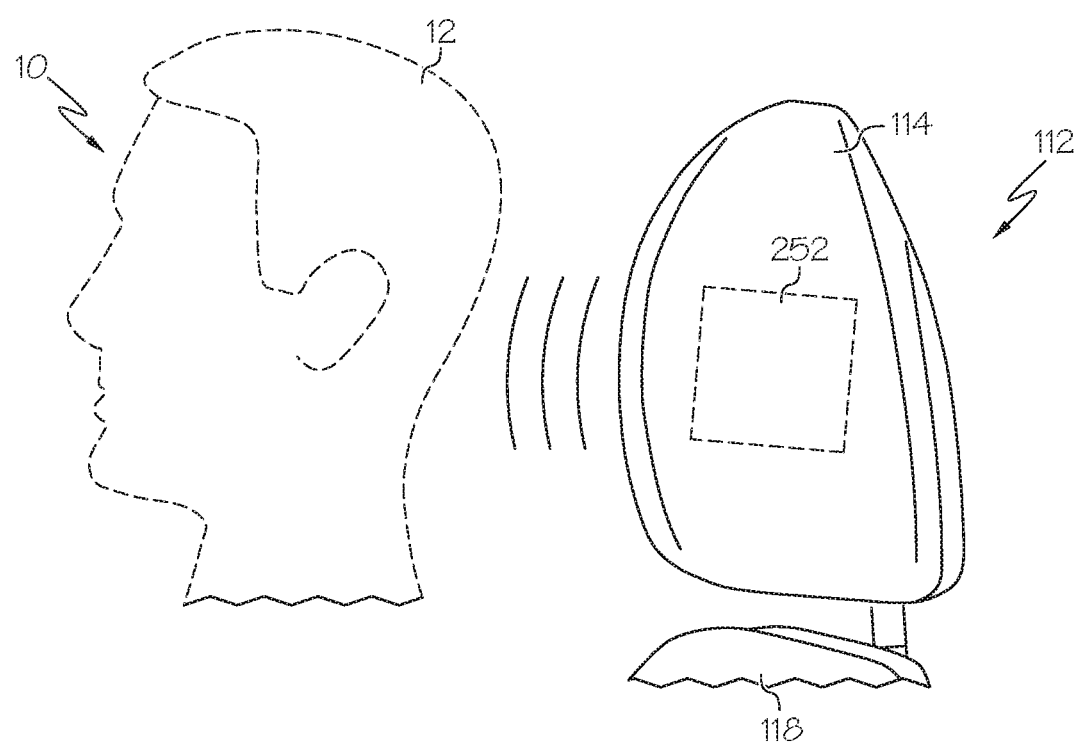
FIG. 5 schematically depicts a side view of the driving support system of FIG. 1 detecting brainwave signals of an occupant according to one or more embodiments shown and described herein.

Still referring to FIG. 1, the one or more sensors 250 may generally include the various sensors described herein, including, for example, one or more neuroimaging sensors 252 capable of detecting brainwave signals of an occupant of the vehicle 110. As discussed in more detail herein, the one or more neuroimaging sensors 252 may comprise magnetoencephalography (MEG) sensors that are capable of detecting the brainwave signals of an occupant in a non-invasive manner, and in particular without requiring direct physical contact between the MEG sensors 252 and a head of the occupant (FIG. 5). It should be understood that the one or more neuroimaging sensors 252 may comprise various other non-invasive, contactless sensors that are configured to detect brainwave signals without requiring physical contact, connection, or engagement with the subject being monitored. The one or more sensors 250 may also include positioning sensors capable of detecting a position of an occupant within the vehicle 110, and in particular a head orientation of the occupant. The positioning sensors may include, for example, one or more imaging sensors 254 and/or one or more pressure sensors 256. The one or more imaging sensors 254 may be capable of detecting a position of an occupant within the vehicle 110 by capturing an image of a passenger cabin of the vehicle 110 to determine a position of the occupant and/or a head orientation of the occupant relative to the cabin or sensors 250. The one or more pressure sensors 256 may be capable of detecting a position of an occupant within the vehicle 110 by detecting a force applied thereto by an occupant seated within the cabin of the vehicle 110 to determine a position of the occupant and/or a head orientation of the occupant relative to the cabin or sensors 250. The one or more sensors 250 may receive sensed information and transmit signals and/or data corresponding to the sensed information to one or more components described herein.

Figure 6:
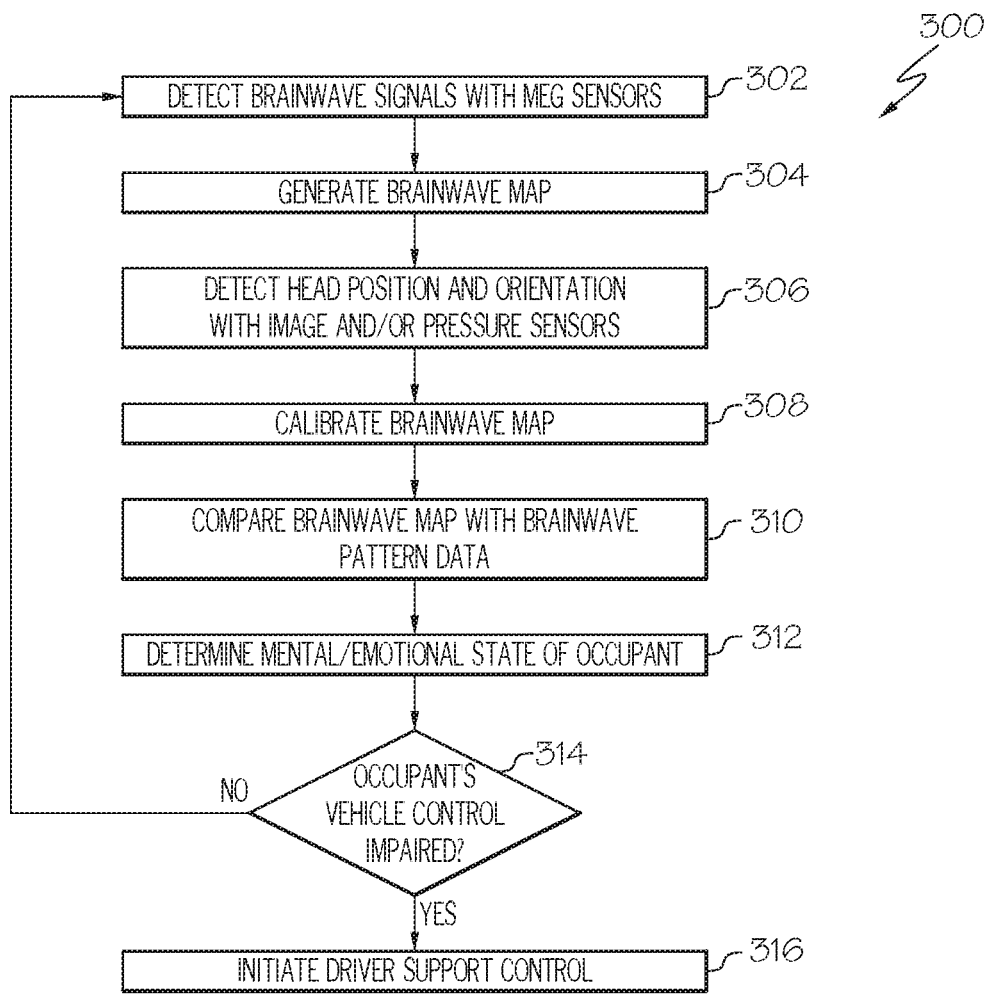
FIG. 6 depicts a flow diagram of an illustrative method of initiating driver support control with the driving support system of FIG. 1 according to one or more embodiments shown and described herein.

For example, the one or more sensors 250, and in particular the neuroimaging sensor 252 may receive brainwave signal data and generate one or more signals and/or data to transmit to the processing device 205 for processing the data and generating a brainwave map of the occupant for purposes of determining a corresponding vehicle support control to initiate (FIG. 6); for determining an identity of an occupant seated within the vehicle 110 (FIG. 9); for transmitting communications to an occupant at an optimal modulation frequency (FIG. 10), and/or the like. By way of further example, the one or more sensors 250, and in particular the imaging sensor 254 and/or the pressure sensor 256, may receive images and/or force data, respectively, and generate one or more signals and/or data to transmit to the processing device 205 for processing the data and calibrating the brainwave map generated by the driver support system 100 for purposes of accurately initiating a vehicle support control or measure based on a present mental state of an occupant (FIG. 6).

Figure 2:
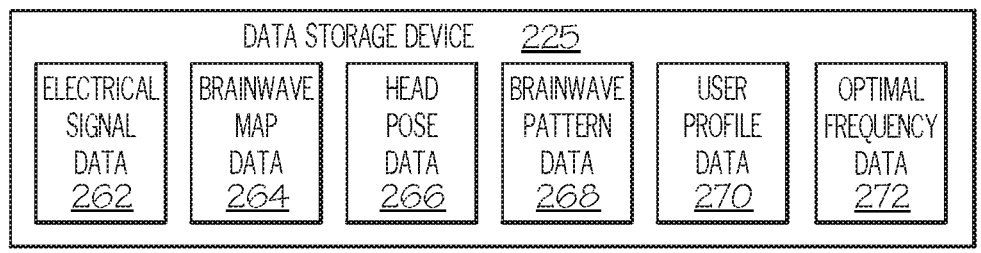
FIG. 2 schematically depicts an illustrative data storage device of the driver support system of FIG. 1 containing illustrative data components according to one or more embodiments shown and described herein.

FIG. 2 schematically depicts a block diagram of various data that may be stored within a storage device (e.g., the data storage device 225) of the driver support system 100, a computing device, and/or a vehicle component according to one or more embodiments shown and described herein. The data storage device 225 may include, for example, electrical signal data 262, brainwave map data 264, head pose data 266, brainwave pattern data 268, user profile data 270, and/or optimal frequency data 272. It should be understood that less, additional, or different data may be stored. Electrical signal data 262 may include, for example, neural oscillation data (i.e., brainwave signal data) detected by the neuroimaging sensor 252 and associated with a particular occupant seated proximate to the neuroimaging sensor 252. Brainwave map data 264 may generally refer to information relating to sensed characteristics by the one or more neuroimaging sensors 252, such as, for example, a brainwave map generated by the driver support system 100, and in particular the brainwave mapping logic 244, based on the electrical signal data 262 collected by the one or more neuroimaging sensors 252 via the brainwave detection logic 242. Head pose data 266 may generally refer to information relating to sensed characteristics by the one or more positioning sensors (i.e., the imaging sensors 254, the pressure sensors 256, and the like), such as, for example, position data of an occupant of the vehicle 110 or head pose data of an orientation of an occupant's head relative to the one or more neuroimaging sensors 252.

Brainwave pattern data 268 may further refer to a database of stored information relating to registered brainwave signals (i.e., stored neural oscillations or rhythmic patterns of neural activity) of one or more occupants of the vehicle 110 that have been previously stored in the driver support system 100, for purposes of facilitating future instances of identifying a returning occupant of the vehicle 110. User profile data 270 may refer to a database of stored information relating to particular system setting preferences of various vehicle components or devices, such as, for example, the user interface hardware 215, the vehicle systems control hardware 230, and the like, for an occupant of the vehicle 110 having a registered user profile stored in the driver support system 100. The optimal frequency data 272 may generally refer to information relating to sensed characteristics by the one or more neuroimaging sensors 252 (e.g., neural oscillation data), such as, for example, an optimal modulation frequency for transmitting communications to a particular occupant as generated by the driver support system 100, and in particular the optimal frequency communication logic 249, based on the electrical signal data 262 collected by the one or more neuroimaging sensors 252 via the brainwave detection logic 242.

Figure 3:
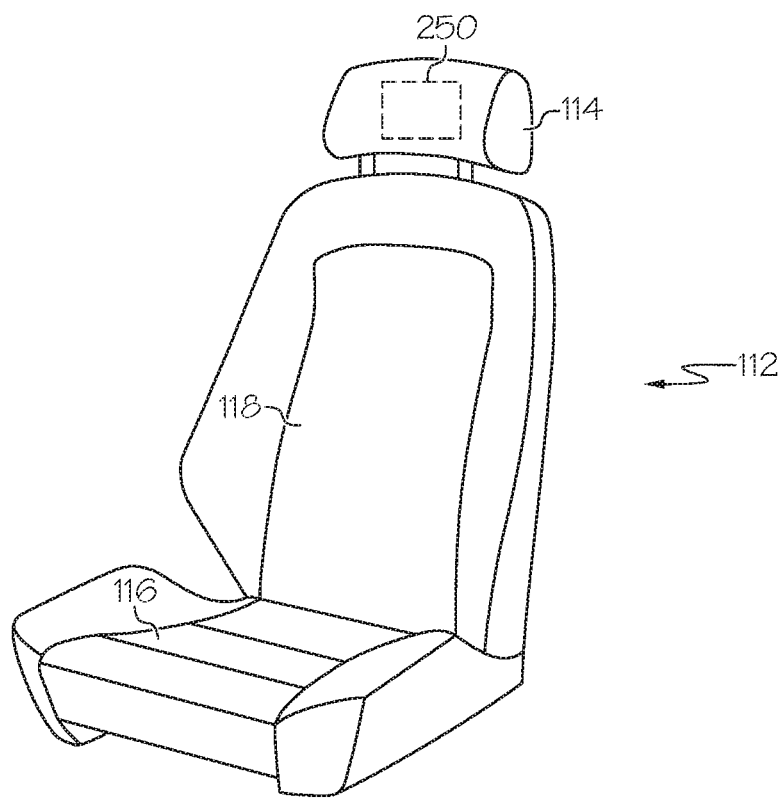
FIG. 3 schematically depicts a perspective view of the driver support system of FIG. 1 embedded within a vehicle headrest according to one or more embodiments shown and described herein.

Referring now to FIG. 3, the one or more sensors 250 of the driver support system 100 are configured to be positioned within the vehicle 110. In particular, the one or more sensors 250 are positioned within the vehicle 110 at a location adjacent to but relatively distal from an occupant of the vehicle 110 such that at least one of the one or more sensors 250 of the driver support system 100 (e.g., the neuroimaging sensors 252) may be positioned at a non-invasive location generally separated (i.e., disengaged) from directly contacting an occupant of the vehicle 110. As one non-limiting example, the one or more sensors 250 of the driver support system 100 are positioned within a seat 112 of the vehicle 110, and in particular, embedded within a headrest 114 of the seat 112. In this instance, the one or more sensors 250, such as, for example, one or more neuroimaging sensors 252, imaging sensors 254, and/or pressure sensors 256, are positioned adjacent to an occupant received along the seat 112 but are non-invasive as they are not in continuous contact with the occupant. In other words, it should be understood that despite the headrest 114 of the seat 112 being positioned generally adjacent to an occupant seated thereon, and in particular to a head of an occupant received on the seat 112, the occupant's head is generally not positioned in direct contact with the headrest 114 of the seat 112 during use of the vehicle 110 by the occupant.

In instances where the driver support system 100 includes a positioning sensor in the form of the imaging sensor 254, the imaging sensor 254 may be positioned along various regions of the seat 112 that may capture image data of an occupant received on the seat 112. As one non-limiting example, the imaging sensor 254 is configured to sense a physical position and/or orientation of an occupant by obtaining an image of the occupant on the seat 112. The imaging sensor 254 may be generally positioned at a location that is adjacent to and not in direct contact with an occupant. For example, the imaging sensor 254 may be positioned in the headrest 114 of the seat 112 to detect an orientation of a head of the occupant, in a ceiling of the vehicle 110 positioned relatively above the seat 112 to detect a pose and/or position of the occupant, along a dashboard or front windshield of the vehicle 110 positioned relatively in front of the seat 112, and/or other suitable locations relative to the seat 112. In instances where the driver support system 100 includes a positioning sensor in the form of the pressure sensor 256, the pressure sensor 256 may be positioned along various regions of the seat 112 that may receive a force applied thereon by an occupant seated on the seat 112. As one non-limiting example, the pressure sensor 256 is configured to sense a physical force applied thereto such that the pressure sensor 256 may be generally positioned at a location that is adjacent to and in direct contact with an occupant. For example, the pressure sensor 256 may be positioned along a base 116 of the seat 112, a back support 118 of the seat 112, one or more armrests of the seat 112, the headrest 114, and/or other regions of the seat 112.

Figure 4:
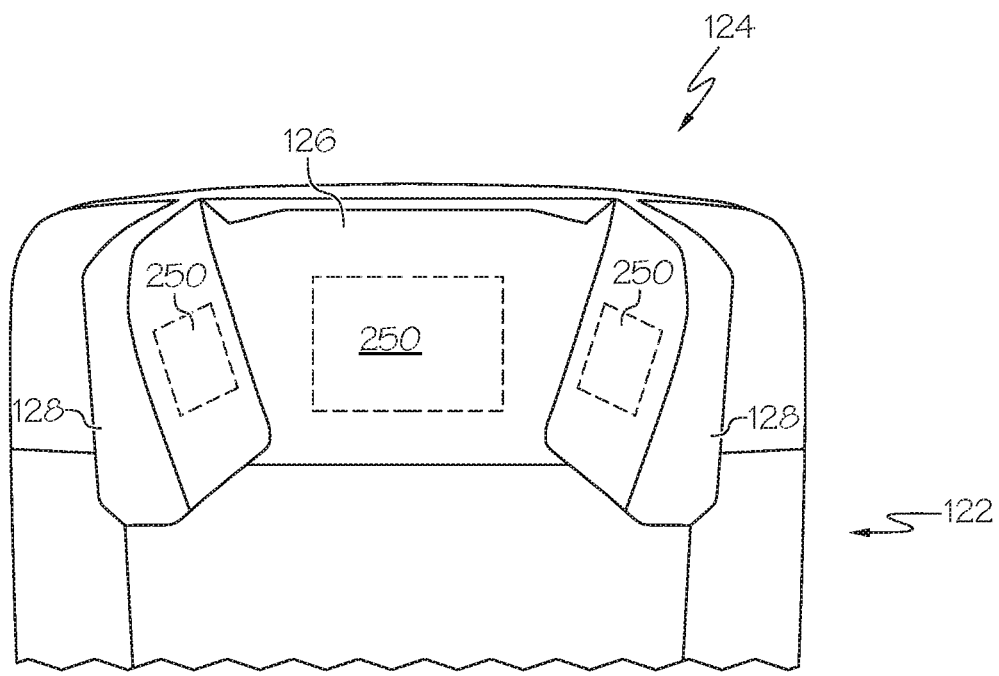
FIG. 4 schematically depicts a perspective view of the driving support system of FIG. 1 embedded within another vehicle headrest including adjustable side panels according to one or more embodiments shown and described herein.

Referring now to FIG. 4, in other embodiments a seat 122 of the vehicle 110 may include a headrest 124 that comprises one or more panels, such as, for example, a center panel 126 disposed between a pair of adjustable side panels 128. The pair of adjustable side panels 128 of the headrest 124 may be configured to selectively move (i.e., pivot) relative to the center panel 126 such that an occupant of the vehicle 110 may reposition the pair of adjustable side panels 128 at varying orientations and/or positions. As described in more detail herein, the pair of adjustable side panels 128 may be moved to improve a position of one or more sensors 250 positioned thereon relative to a head of an occupant received on the seat 122. Improving a position of the one or more sensors 250 may provide enhanced detection of sensed characteristics by the one or more sensors 250, improved accuracy of the data recorded from the one or more sensors 250, and the like.

The one or more panels of the headrest 124 may include one or more sensors 250 disposed (i.e., embedded) therein. The pair of adjustable side panels 128 of the headrest 124 may further provide an adjustable surface for the one or more sensors 250 to be positioned along to enhance an accuracy of sensing the characteristics of an occupant received on the seat 122. For example, the one or more adjustable side panels 128 may include the imaging sensor 254 positioned thereon such that the imaging sensor 254 may be configured to capture a side image of the occupant's head to determine whether the occupant's head is directed directly toward a front windshield of the vehicle 110 or at various other directions other than the front windshield.

Additionally or alternatively, the one or more adjustable side panels 128 may include the pressure sensor 256 positioned thereon such that the pressure sensor 256 may be configured to sense a force applied thereto by the occupant's head. In this instance, the pressure sensor 256 may detect a change in orientation of the occupant's head from, for example, a forward direction directed toward a front windshield of the vehicle 110 to another direction offset from the forward direction, in response to sensing a force received along the one or more side panels 128. In other embodiments, the driver support system 100 may further include one or more pressure sensors 256 positioned within the base 116 and/or the back support 118 of the seat 112. In this instance, the pressure sensor 256 may be configured to detect a force applied thereto, and in particular a change in force from a muscle of the occupant at the respective body location (e.g., gluteus muscle, piriformis muscle, extensor muscle, and the like). For example, the driver support system 100, and in particular the calibration logic 246, may be configured to correlate a movement of a bodily muscle of the occupant along the base 116 and/or the back support 118 to a change in orientation and/or position of the occupant relative to the passenger cabin of the vehicle 110.

It should be understood that the headrests 114, 124 discussed above may include one or more sensors 250 embedded therein, and in particular, may include one or more neuroimaging sensors 252, one or more of imaging sensors 254, and/or one or more pressure sensors 256. It should further be understood that the driver support system 100 may include other sensors, devices, and/or mechanisms other than the neuroimaging sensors 252, imaging sensors 254, or pressure sensors 256 detailed above for performing the functions described herein such that the sensors 250 depicted and described herein are merely illustrative examples.

Referring now to FIG. 5, and as briefly described above, the one or more neuroimaging sensors 252 (e.g., magnetoencephalography (MEG) sensor) of the driver support system 100 may be capable of detecting brainwave signals of an occupant 10 of the vehicle 110 in a non-invasive manner without physically contacting the occupant 10. In particular, with the neuroimaging sensors 252 positioned within the headrest 114 of the seat 112, the neuroimaging sensors 252 are configured to be positioned distally from a head 12 of the occupant 10 such that the neuroimaging sensors 252 are adjacent to the occupant 10 but not engaged with the occupant 10. In this instance, the one or more neuroimaging sensors 252 may include a detection field that includes a range determined based on numerous factors, including, for example, a size of the neuroimaging sensors 252, a quantity of neuroimaging sensors 252 in the vehicle 110, a location of the neuroimaging sensors 252 relative to the occupant 10, and the like. Accordingly, due to the location of the neuroimaging sensors 252 within the headrest 114 of the seat 112 in one non-limiting example, the one or more neuroimaging sensors 252 are capable of detecting neurological signals of the occupant 10 seated on the seat 112 due to the neuroimaging sensors 252 being positioned adjacent to the head 12 of the occupant 10 despite being disengaged from physically contacting the occupant 10. In other words, with the headrest 114 including the one or more neuroimaging sensors 252 embedded therein and positioned proximate to the head 12 of an occupant 10 received on the seat 112, the one or more neuroimaging sensors 252 may non-invasively detect the brainwave signals of the occupant 10 without contact since the head 12 of the occupant 10 is within a detection field of the neuroimaging sensors 252. By way of example only, the one or more neuroimaging sensors 252 may have a detection field ranging from about 1 inch to about 6 inches. It should be understood that a detection field of the one or more neuroimaging sensors 252 may vary in accordance with various factors including at least those described above.

It should be understood that the components illustrated in FIGS. 1-2 of the driver support system 100 are merely illustrative and are not intended to limit the scope of this disclosure. More specifically, while the components of the driver support system 100 in FIGS. 1-2 are illustrated as residing within the vehicle 110 and along a seat 112, 122 in FIGS. 3-5, this is a nonlimiting example. In some embodiments, one or more of the components may reside external to the driver support system 100, the seat 112, 122, and/or the vehicle 110. As mentioned above, the various components described with respect to FIGS. 1-2 may be used to carry out one or more processes and/or provide functionality for providing driver support or assistance via the driver support system 100, for identifying an identify of an occupant of the vehicle 110, for uploading stored vehicle system preferences to the vehicle 110 based on an identity of the occupant, for transmitting communications to an occupant of the vehicle 110 at an optimal modulation frequency, and/or the like. Illustrative examples of the various processes are described with respect to FIGS. 6, 8 and 10-11 herein below, which may generally be completed by the driver support system 100 or a component thereof, such as, for example, the processing device 205 (FIG. 1).

Referring now to FIG. 6, an illustrative method of generating a brainwave map of an occupant of the vehicle 110 for purposes of determining a corresponding vehicle support control to initiate based on a mental and/or emotional state of the occupant, generally designated 300, is depicted according to some embodiments. The various steps described with respect to FIG. 6 are merely illustrative, and additional, fewer, or alternative steps are contemplated without departing from the scope of the present disclosure. It should be understood that in some embodiments, the driver support system 100 is not configured to autonomously initiate a driver support control or measure to the vehicle 110. In addition, the steps described with respect to FIG. 6 are generally completed when the vehicle 110 is being actively operated (i.e., moving).

As one non-limiting example, an occupant of the vehicle 110 may enter a passenger cabin of the vehicle 110 and sit on one of the seats 112, 122 therein, such as, for example, the seat 112, 122 corresponding to a driver of the vehicle 110. As the occupant actively operates the vehicle 110, the occupant is positioned on the seat 112, 122 with a head of the occupant located relatively proximate to the headrest 114, 124 of the seat 112, 122 (FIG. 5). In this instance, the occupant experiences neural activity within a central nervous system of the occupant's body, and in particular, within a head of the occupant. The brainwave signals (i.e., synchronized electrical pulses) transmitted between the cells of the occupant's brain generally arise from feedback connections between masses of neurons communicating with one another. Depending on a brainwave frequency, as measured in Hertz (i.e., cycles per second), the brainwave signals may be divided into bands delineating slow, moderate, and fast brainwaves. It should be understood that brainwave frequency contributes to a state of mind such that measuring a frequency of the brainwave signals of an occupant is indicative of determining an occupant's present state of mind. With the headrest 114, 124 of the seat 112, 122 including one or more sensors 250 therein (FIGS. 3-5), and in particular, at least one neuroimaging sensor 252 (e.g., MEG sensor), the brainwave signals of the occupant may be detected by the driver support system 100 included in the vehicle 110.

Still referring to FIG. 6, at step 302, the one or more programming instructions included in the memory component 240, such as the brainwave detection logic 242, when executed by the processing device 205, causes the processing device 205 to initiate the one or more sensors 250 capable of sensing brainwave signals from an area adjacent to the headrest 114, 124 of the seat 112, 122. In particular, the neuroimaging sensor 252 of the driver support system 100 actively detects any brainwave signals within a detection field of the neuroimaging sensor 252. The brainwave detection logic 242, when executed by the processing device 205, causes the processing device 205 to record the brainwave signals and store the corresponding electrical signal data 262 in the data storage device 225 of the driver support system 100.

At step 304, the one or more programming instructions included in the memory component 240, such as the brainwave mapping logic 244, when executed by the processing device 205, causes the processing device 205 to perform a neuro mapping procedure (i.e., brain mapping) to map the brainwave signals of the occupant. The brainwave map generated by the processing device 205, when executing the brainwave mapping logic 244, provides a brainwave pattern report of the occupant for purposes of allowing an identification of the brainwave patterns of the occupant as the occupant operates the vehicle 110. It should be understood that depending on a location of the one or more neuroimaging sensors 252 within the vehicle 110 (e.g., within the headrest 114, 124) and relative to a head of the occupant, different regions of an occupant's brain may be analyzed and mapped (e.g., frontal lobe, parietal lobe, central lobe, temporal lobe, occipital lobe, and the like). It should further be understood that analyzing the brainwave patterns at the various regions of an occupant's brain may be indicative of different characteristics presently experienced by the occupant. For example, an occupant experiencing similar brainwave patterns at two different regions of the occupant's brain (e.g., frontal lobe, parietal lobe, central lobe, temporal lobe, occipital lobe) may indicate distinct information relating to a present mental state and/or emotional condition of the occupant. Accordingly, accurately attributing detected brainwave patterns to the region of a brain from which the brainwave patterns originate from is vital for effectively identifying a present mental state of the occupant.

Still referring to FIG. 6, the brainwave maps generated by the driver support system 100 (i.e., brainwave pattern reports), in response to the processing device 205 executing the brainwave mapping logic 244, provides information relating to the brainwave signals experienced by an occupant. As briefly described above, the brainwave pattern reports are indicative of a state of mind of an occupant. Accordingly, the brainwave mapping logic 244 of the driver support system 100 generates a brainwave map from the electrical signal data 262 retrieved from the occupant via the one or more neuroimaging sensors 252. Depending on a brainwave pattern and/or a brainwave signal frequency, a mental and/or emotional state of the occupant may be determined (e.g., amusement, awe, gratitude, hope, inspiration, interest, joy, love, pride, serenity, and the like). As described in more detail herein, the brainwave mapping logic 244 of the driver support system 100, when executed by the processing device 205, causes the processing device 205 to analyze the brainwave map generated for the occupant to determine patterns of the brainwave signals presently experienced by the occupant to thereby determine a corresponding mental state of the occupant.

It should be understood that a position and orientation of the occupant, and in particular a head of the occupant relative to a passenger cabin of the vehicle 110, may continuously change and vary during an operation of the vehicle 110 while the one or more neuroimaging sensors 252 detect brainwave signals originating from the occupant's head. Accordingly, the electrical signal data 262 recorded from the one or more neuroimaging sensors 252, and utilized by the brainwave mapping logic 244 to generate the brainwave map, may require adjustment to ensure the brainwave map is accurately generated. As briefly described above, depending on the particular region of the occupant's brain where a brainwave signal is detected (e.g., frontal lobe, parietal lobe, central lobe, temporal lobe, occipital lobe), distinct information relating to a present mental state and/or emotional condition of the occupant may be determined. Accordingly, accurately analyzing the brainwave map generated by the driver support system 100 requires calibrating (i.e., reorienting) the brainwave map in accordance with the relative positional data of the head of the occupant when the electrical signal data 262 is recorded.

Still referring to FIG. 6, at step 306, the one or more programming instructions included in the memory component 240, such as the calibration logic 246, when executed by the processing device 205, causes the processing device 205 to initiate the one or more sensors 250 capable of sensing a position or orientation of an occupant relative to the vehicle 110 and/or the one or more sensors 250. In particular, positioning sensors in the form of one or more imaging sensors 254 and/or pressure sensors 256 of the driver support system 100 actively detect a position of the occupant on the seat 112, 122, and in particular an orientation of a head of the occupant relative to a passenger cabin of the vehicle 110, the headrest 114, 124 of the seat 112, 122, and/or a location of the one or more neuroimaging sensors 252. An orientation of a head of an occupant may be determined by sensing characteristics relating to a profile of the head, facial features of the head, and the like. The calibration logic 246, when executed by the processing device 205, further causes the processing device 205 to record positional data, such as, for example, the head pose data 266, and store the corresponding head pose data 266 in the data storage device 225 of the driver support system 100.

In this instance, the brainwave map generated by the brainwave mapping logic 244 from the electrical signal data 262 detected by the neuroimaging sensors 252 is calibrated relative to the head pose data 266 generated by the calibration logic 246 as detected by the imaging sensors 254 and/or pressure sensors 256. Calibrating the brainwave map with the head pose data 266 includes adjusting an orientation, position, shape, size, and the like of the brainwave map in accordance with the orientation, position, shape, and size of a head of the occupant based on an actual position of the occupant when the electrical signal data 262 utilized to generate the brainwave map is recorded. As briefly described above, accurately attributing detected brainwave patterns to the region of a brain from which the brainwave patterns originate from provides for effectively identifying a present mental state of the occupant. Accordingly, the generated brainwave map is calibrated pursuant to step 306 described above to ensure the brainwave signals represented in the brainwave map generated at step 304 are accurately depicted.

Still referring to FIG. 6, at step 310, the brainwave mapping logic 244, when executed by the processing device 205, further causes the processing device 205 to analyze the calibrated-brainwave map to determine the brainwave patterns reported thereon. In some embodiments, determining a frequency of the brainwave signals in conjunction with the brainwave pattern data at the respective regions of the occupant's brain may be indicative of a mental state and/or emotional condition of the occupant. The brainwave mapping logic 244, when executed by the processing device 205, further causes the processing device 205 to compare the brainwave patterns and signal frequencies to the brainwave pattern data 268 stored in the data storage device 225 of the driver support system 100. The brainwave pattern data 268 generally includes stored information relating to particular mental states and/or emotional conditions corresponding to brainwave patterns and/or brainwave signal frequencies. As merely an illustrative example, the brainwave pattern data 268 of the driver support system 100 may include information attributing certain brainwave patterns with brainwave signal frequencies ranging from about 40 Hertz or greater (i.e., cycles per second) as being categorized within a Gamma Band, which may generally be indicative of an occupant being in a state of high-level information processing; and other brainwave patterns with brainwave signal frequencies ranging from about 14 to 40 Hertz as being categorized within a Beta Band, which may generally be indicative of an occupant being in a state of active consciousness and reasoning.

Further, the brainwave pattern data 268 may attribute certain brainwave patterns with brainwave signal frequencies ranging from about 7.5 Hertz to about 14 Hertz as being categorized within an Alpha Band, which may generally be indicative of an occupant being in a state of deep relaxation; and other brainwave patterns with brainwave signal frequencies ranging from about 4 Hertz to about 7.5 Hertz as being categorized within a Theta Band, which may generally indicative of an occupant being in a state of light meditation and slight drowsiness. Lastly, the brainwave pattern data 268 may include information attributing particular brainwave patterns with brainwave signal frequencies ranging from about 0.5 Hertz to about 4 Hertz as being categorized within a Low Alpha Band and/or Delta Band, which may generally be indicative of an occupant being in a state of unconsciousness and deep sleep. It should be understood that the exemplary brainwave patterns, brainwave signal frequencies and corresponding categorizations described herein are merely provided for illustrative purposes only such that additional and/or fewer brainwave patterns, brainwave signal frequency ranges and corresponding mental/emotional states may be stored within the brainwave pattern data 268.

Still referring to FIG. 6, at step 312, the brainwave mapping logic 244 when executed by the processing device 205 further causes the processing device 205 to identify the corresponding mental state and/or emotional condition of the occupant based on the brainwave map data 264 of the occupant in comparison to the brainwave pattern data 268. In this instance, at step 314, with the mental state of the occupant identified by the driver support system 100, the processing device 205 executes the driving support logic 247 to determine whether the occupant's control of the vehicle 110 is impaired, inhibited, influenced, and/or the like based on the detected mental state of the occupant. For example, if the present mental state of the occupant is indicative of a partially unconscious state (e.g., drowsiness), the driving support logic 247 may determine that the occupant's control of the vehicle 110 is at least partially impaired at step 314 such that the driver support system 100 proceeds to step 316 wherein the processing device 205 causes, when executed by the driving support logic 247, initiation of a corresponding driver support control measure that is particularly directed to address the partially unconscious state of the occupant and assist operation of the vehicle 110.

By way of example, the driver support control measure may be in the form of actuating a notification along one or more of the user interface hardware 215 (e.g., display output hardware, audio output hardware, and the like), influencing operation of the one or more mobility control hardware 220 (e.g., steering wheel, gas or brake pedal, wheels, and the like), controlling one or more of the vehicle systems control hardware 230 (e.g., HVAC system, a position and/or height of a seat of the vehicle 110, a window of the vehicle 110, and the like), and the like. It should be understood that in other examples, depending on the identified mental state of the occupant that is determined to have at least partially impaired the occupant's effective control or operation of the vehicle 110, the driving support logic 247 provides for a corresponding driver support control measure to be executed by the processing device 205 at step 316 that is specifically configured to improve the occupant's mental/emotional state and/or the occupant's control of the vehicle 110 relative to the present state of mind of the occupant.

Alternatively, at step 314, in response to determining that the vehicle control by the occupant is not impaired, influenced, inhibited or the like based on the determined mental state of the occupant, the process 300 proceeds to step 302 to reinitiate detection of the brainwave signals originating from the occupant as the occupant continues to operate the vehicle 110. It should be understood that the driver support system 100 of the present example may continue to continuously perform the process 300 described above while the vehicle 110 is in continued operation. In other embodiments, the driver support system 100 may be configured to perform the process 300 at predetermined intervals during operation of the vehicle 110 such that the driver support system 100 periodically determines a mental state of the occupant.

Figure 7:
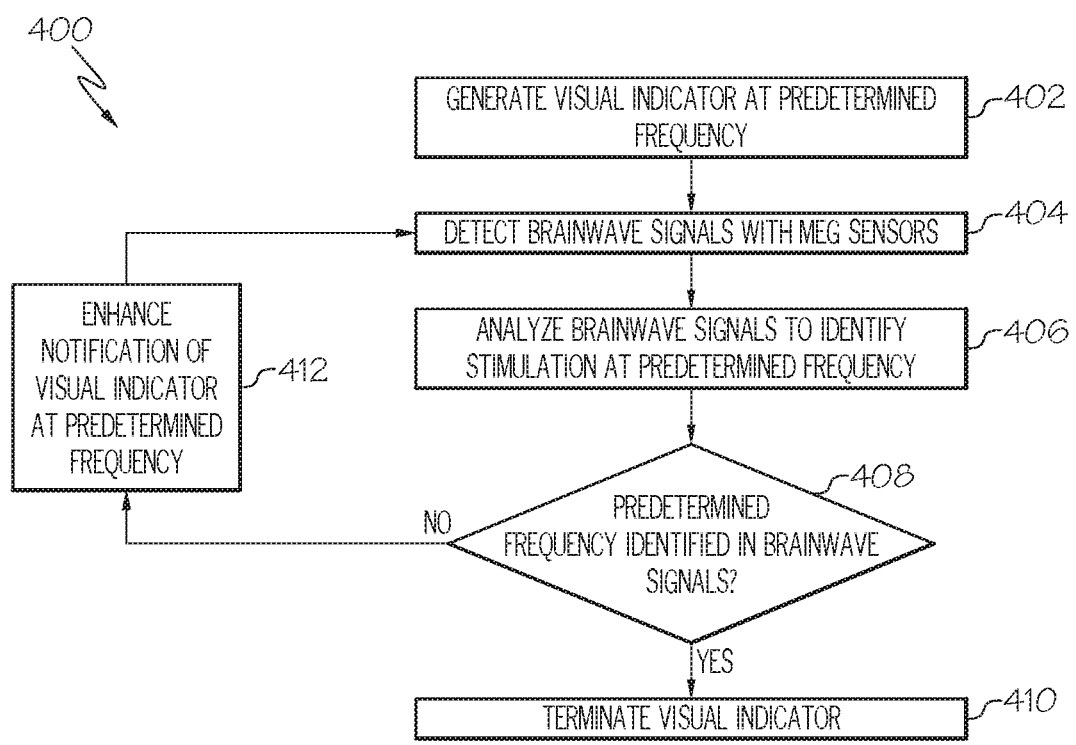
FIG. 7 depicts a flow diagram of another illustrative method of initiating driver support control with the driving support system of FIG. 1 according to one or more embodiments shown and described herein.

Referring now to FIG. 7, an illustrative method of visual cortex stimulation is depicted where a visual indicator may be generated within the vehicle 110 for directing an attention of an occupant to the corresponding visual indicator, generally designated 400, according to some embodiments. The various steps described with respect to FIG. 7 are merely illustrative, and additional, fewer, or alternative steps are contemplated without departing from the scope of the present disclosure. It should be understood that in some embodiments, the driver support system 100 is not configured to autonomously initiate a driver support control or measure (i.e., a visual indicator) to the vehicle 110. In addition, the steps described with respect to FIG. 7 are generally completed when the vehicle 110 is in active operation.

As one non-limiting example, as the vehicle 110 is being actively operated, one or more items or objects requiring an attention of an occupant of the vehicle 110 may be present, an identification of which may be of noteworthy significance for the one or more occupants of the vehicle 110 to ensure an awareness of the vehicle's 110 surroundings and/or condition of operation. For instance, items or objects external to the vehicle 110 may be present within a predetermined proximity of the vehicle 110, such as, for example, a pedestrian, bicyclist, vehicle, traffic light, road median, traffic sign, and/or the like which may be encountered during operation of the vehicle 110. Further, items or objects internal to the vehicle 110 may also be present, such as, for example, a fuel gauge, an engine temperature gauge, a speedometer alert, a global positioning system (GPS) notification, and/or the like which may be encountered during operation of the vehicle 110.

As the occupant actively operates the vehicle 110, the occupant may be positioned on the seat 112, 122 with a head of the occupant located relatively proximate to the headrest 114, 124 of the seat 112, 122. The occupant may experience neural activity within a central nervous system of the occupant's body, and in particular, within a head of the occupant where the brain is located. With the headrest 114, 124 of the seat 112, 122 including one or more sensors 250 therein (FIGS. 3-5), and in particular, at least one neuroimaging sensor 252 (e.g., MEG sensor), the brainwave signals of the occupant may be detected by the driver support system 100 as the visual indicators are generated within the vehicle 110 by the driver support system 100.

Still referring to FIG. 7, at step 402, the one or more programming instructions included in the memory component 240, such as the driving support logic 247, when executed by the processing device 205, causes the processing device 205 to generate one or more visual indicators within the vehicle 110. In particular, the driving support logic 247 causes the processing device 205 to generate the one or more visual indicators at one or more locations of the vehicle 110 that correspond to a relative location of a target object that is to be identified by the occupant. For instance, the one or more visual indicators may be generated via the user interface hardware 215, the vehicle systems control hardware 230, and the like. Further, the driving support logic 247 causes the processing device 205 to generate the one or more visual indicators at predetermined frequencies (e.g., 8.5 Hertz, 10 Hertz, 12 Hertz, 15 Hertz, and the like) that vary relative to one another such that the visual indicators flash at varying frequencies from one another. It should be understood that the visual indicators may be generated along various surfaces of the vehicle 110 at a location where a corresponding target object may be identified by an occupant.

Figure 8:
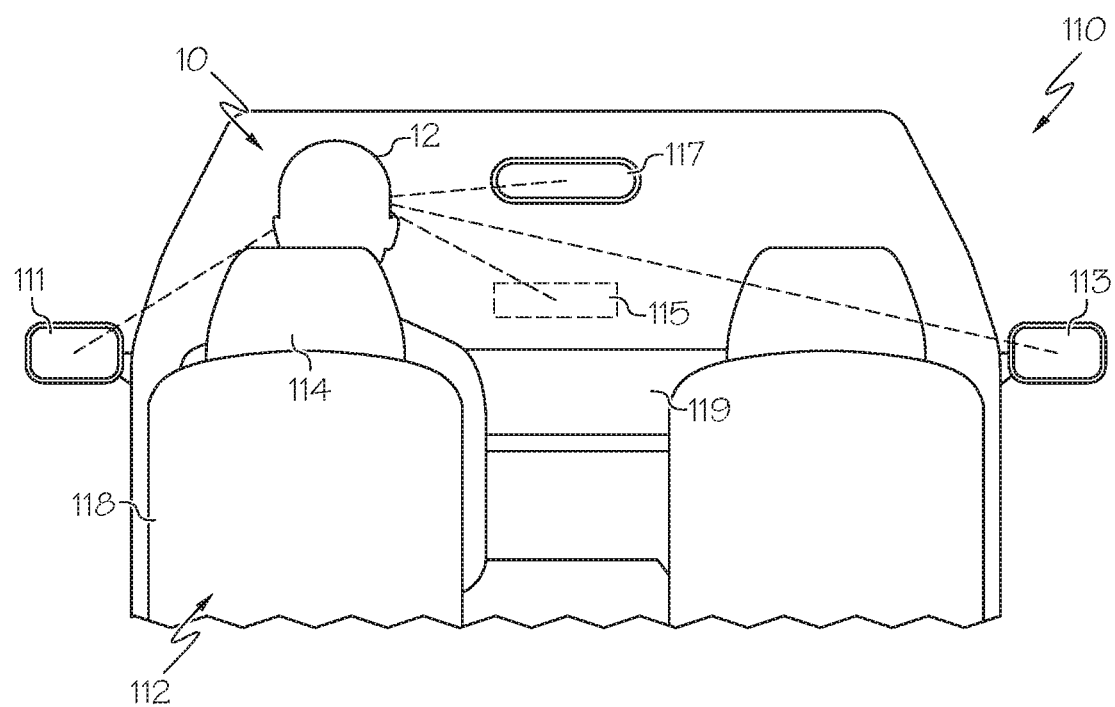
FIG. 8 schematically depicts visual indicators displayed along a vehicle heads-up display and multiple mirrors of the vehicle with the driver support system of FIG. 1 according to one or more embodiments shown and described herein.

Referring now to FIG. 8, the visual indicators may be generated along various surfaces of the vehicle 110, including, for example, the display output hardware of the user interface hardware 215, the components of various vehicle systems control hardware 230, and the like. As one non-limiting example, the visual indicators are generated on display output hardware of the user interface hardware 215, such as, for example, a heads-up display (HUD) of a front windshield 115 of the vehicle 110, a side mirror 111, 113 of the vehicle 110, a rearview mirror 117 of the vehicle 110, a dashboard display 119 of the vehicle 110, side and rear windows of the vehicle 110, and the like. It should be understood that the visual indicators may be provided to an occupant of the vehicle 110 via various other devices, systems, hardware, and surfaces of the vehicle 110.

Referring back to FIG. 7, at step 404, the one or more programming instructions included in the memory component 240, such as the brainwave detection logic 242, when executed by the processing device 205, causes the processing device 205 to initiate the one or more sensors 250 capable of sensing brainwave signals from an area adjacent to the headrest 114, 124 of the seat 112, 122. In particular, the neuroimaging sensor 252 of the driver support system 100 actively detects any brainwave signals within a detection field of the neuroimaging sensor 252. The brainwave detection logic 242, when executed by the processing device 205, causes the processing device 205 to record the brainwave signals and store the corresponding electrical signal data 262 in the data storage device 225 of the driver support system 100. Although a calibration of the brainwave signals is not shown and/or described in the process 400 herein, it should be understood that the brainwave signals detected by the neuroimaging sensors 252 of the present example may be calibrated by positional sensors (e.g., imaging sensors 254, pressure sensors 256) similar to those shown and described above with respect to process 300.

At step 406, the driving support logic 247, when executed by the processing device 205, causes the processing device 205 to analyze the electrical signal data 262 detected from the occupant to determine whether the generated visual indicator was identified by the occupant. For example, if a visual indicator is generated along the HUD display of the front windshield 115 of the vehicle 110, the visual indicator will be displayed (e.g., flashed) at a corresponding, predetermined frequency thereon. Accordingly, the brainwave signals originating from the occupant will be stimulated by, and generate an electrical signal corresponding to, the predetermined frequency of the particular visual indicator observed when the occupant detects and processes the flashing visual indicator.

Referring still to FIG. 7, at step 408, the processing device 205 when executing the driving support logic 247 analyzes the electrical signal data 262 to identify whether the particular predetermined frequency of the respective visual indicator (e.g., 8 Hz, 10 Hz, 12 Hz, 15 Hz, etc.) is included therein. In other words, the driving support logic 247 causes the processing device 205 to compare the electrical signal data 262 to the one or more predetermined frequencies of the one or more visual indicators generated for the occupant's attention to confirm the occupant's observation of the respective visual indicators by identifying a stimulation of the brainwave signals detected from the occupant at the predetermined frequency of the visual indicator in the electrical signal data 262. In this instance, in response to confirming that the predetermined frequency corresponding to the visual indicator at step 408 is identified, the process proceeds to step 410 wherein the visual indicator is terminated as the driver support system 100 has confirmed the occupant's recognition of the visual indicator.

Alternatively, at step 412, in response to determining at step 408 that the predetermined frequency corresponding to the visual indicator generated for the occupant's observation was not detected, the driving support logic 247 causes the processing device 205 to control the respective user interface hardware 215 and/or the vehicle systems control hardware 230 that the visual indicator is generated on. In particular, characteristics of the visual indicator may be enhanced to promote a notification and detection of the visual indicator for the occupant's observation. In this instance, the process 400 continues to step 404 where the one or more sensors (i.e., the neuroimaging sensors 252) detect the brainwave signals originating from the occupant to determine whether the visual indicator has since been detected after the amplified development of the visual indicator.

Figure 9:
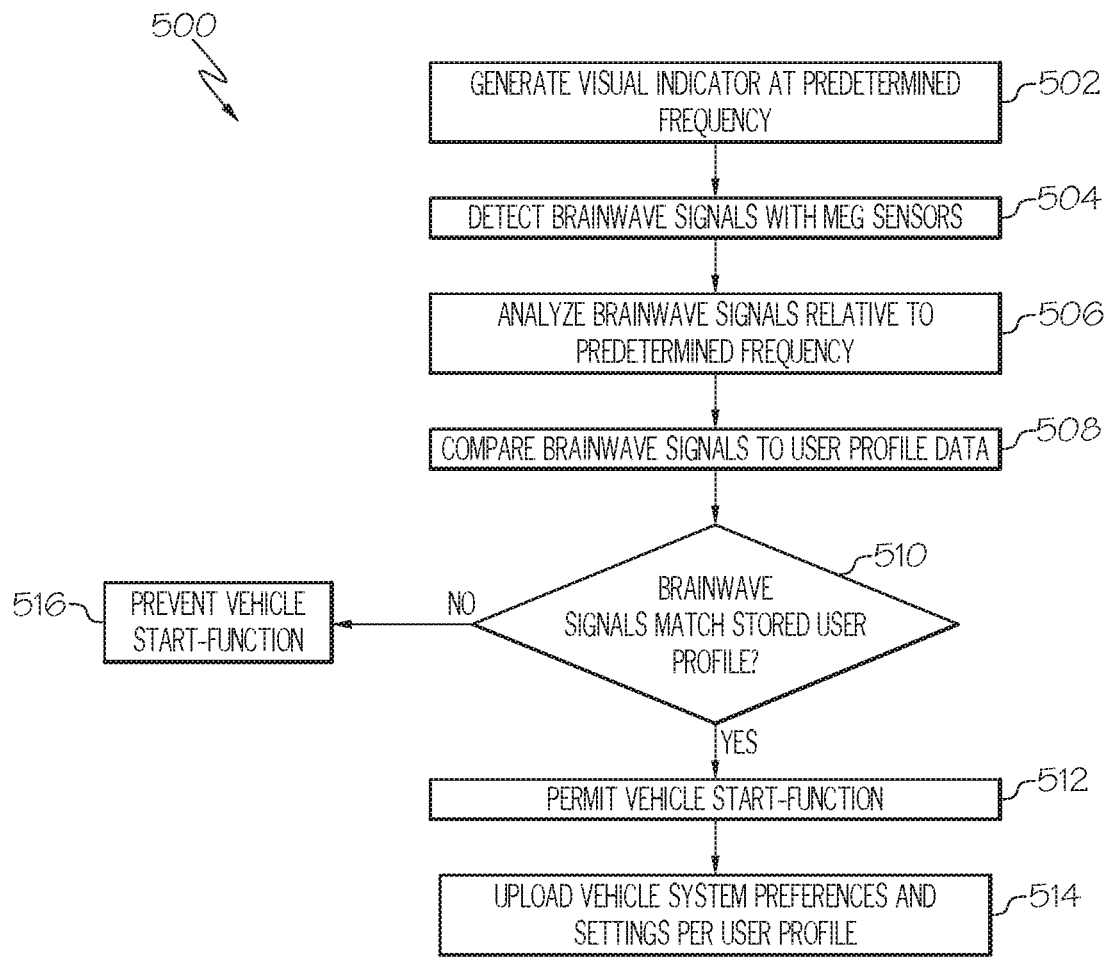
FIG. 9 depicts a flow diagram of another illustrative method of confirming an identity of an occupant of a vehicle with the driving support system of FIG. 1 according to one or more embodiments shown and described herein.

Referring now to FIG. 9, an illustrative method of brainwave signal identification is depicted where an identity of an occupant of the vehicle 110 may be confirmed, generally designated 500, according to some embodiments. The various steps described with respect to FIG. 9 are merely illustrative, and additional, fewer, or alternative steps are contemplated without departing from the scope of the present disclosure. It should be understood that in one non-limiting example, the process 500 is initiated autonomously without requiring a physical actuation and/or physical contact to confirm an identity of an occupant. In some embodiments, the driver support system 100 is not configured to autonomously initiate an identification of an occupant within the vehicle 110 such that actuation of the process 500 may be required. In addition, the steps described with respect to FIG. 9 are generally completed prior to the vehicle 110 being actively operated (i.e., started).

As one non-limiting example, when an occupant initially enters into the vehicle 110 an identity of the occupant may be determined to confirm whether the occupant is authorized to operate the vehicle 110. In particular, an identity of the occupant may be determined by the driver support system 100 by comparing the brainwave signals of the occupant presently located within the vehicle 110 to stored brainwave data (i.e., user profile data 270) corresponding to approved operators of the vehicle 110. The driver support system 100 may include one or more user profiles that, upon determining an identity of an occupant of the vehicle 110 based on a comparative analysis of the brainwave signals of the occupant to the registered brainwave signals stored in one or more user profiles, preprogrammed vehicle system settings may be applied to the various components of the vehicle 110 to promote a convenience and comfort of operating the vehicle 110.

In particular, when initially entering the vehicle 110, the occupant may be positioned on the seat 112, 122 with a head of the occupant located relatively proximate to the headrest 114, 124 of the seat 112, 122. In this instance, the occupant may experience neural activity within a central nervous system of the occupant's body, and in particular, within a head of the occupant. With the headrest 114, 124 of the seat 112, 122 including one or more sensors 250 therein (FIGS. 3-5), and in particular, at least one neuroimaging sensor 252 (e.g., MEG sensor), the brainwave signals of the occupant may be detected by the driver support system 100 as visual indicators are generated within the vehicle 110 by the driver support system 100.

Still referring to FIG. 9, at step 502, the one or more programming instructions included in the memory component 240, such as the driving support logic 247, when executed by the processing device 205, causes the processing device 205 to generate one or more visual indicators within the vehicle 110. In particular, the driving support logic 247 causes the processing device 205 to generate the one or more visual indicators at one or more locations of the vehicle 110. For instance, the one or more visual indicators may be generated via the user interface hardware 215, the vehicle systems control hardware 230, and the like. Further, the driving support logic 247 causes the processing device 205 to generate the one or more visual indicators at predetermined frequencies that vary relative to one another such that the visual indicators are at least partially distinct from one another. It should be understood that the visual indicators may be generated along various surfaces of the vehicle 110 at a location where the indicator may be identified by an occupant, similar to the locations of the vehicle 110 described above and shown in FIG. 8, such as, for example, a rearview mirror 117. It should be understood that the visual indicators may be provided to an occupant of the vehicle 110 via various other devices, systems, hardware, and surfaces of the vehicle 110.

At step 504, the one or more programming instructions included in the memory component 240, such as the brainwave detection logic 242, when executed by the processing device 205, causes the processing device 205 to initiate the one or more sensors 250 capable of sensing brainwave signals from an area adjacent to the headrest 114, 124 of the seat 112, 122. In particular, the neuroimaging sensor 252 of the driver support system 100 actively detects any brainwave signals within a detection field of the neuroimaging sensor 252. The brainwave detection logic 242, when executed by the processing device 205, causes the processing device 205 to record the brainwave signals and store the corresponding electrical signal data 262 in the data storage device 225 of the driver support system 100.

Referring still to FIG. 9, at step 506, the driving support logic 247, when executed by the processing device 205, causes the processing device 205 to analyze the electrical signal data 262 detected from the occupant to initially determine whether the generated visual indicator was identified by the occupant. For example, if a visual indicator is generated along the rearview mirror 117 of the vehicle 110, the visual indicator will be displayed at a predetermined frequency thereon. Accordingly, the brainwave signals originating from the occupant will generate at least an electrical signal at the predetermined frequency of the visual indicator observed by the occupant when the occupant detects and processes the visual indicator. In other words, the processing device 205 when executing the identity confirmation logic 248 analyzes the electrical signal data 262 to identify whether an electrical signal at the predetermined frequency of the respective visual indicator is included therein. Further at step 506, the driving support logic 247, when executed by the processing device 205, causes the processing device 205 to analyze the electrical signal data 262, and in particular the plurality of brainwave signals relative to (i.e., surrounding) the electrical signal at the predetermined frequency such that the electrical signal corresponding to the predetermined frequency serves as a reference indicator for the electrical signal data 262.

At step 508, the identity confirmation logic 248 causes the processing device 205 to compare the relative electrical signal data 262 of the occupant to the user profile data 270 stored within the data storage device 225 to determine whether the occupant of the vehicle 110 is known. In particular, as briefly described above, the user profile data 270 includes stored brainwave data corresponding to approved operators of the vehicle 110 such that the driver support system 100 includes one or more registered user profiles. Accordingly, the electrical signal data 262 of the occupant positioned within the vehicle 110, and in particular the surrounding electrical data 262 relative to the reference indicator (i.e., the brainwave signal corresponding to the predetermined frequency within the electrical signal data 262) is analyzed in comparison to the user profile data 270.

Referring still to FIG. 9, at step 510, the identity confirmation logic 248 causes the processing device 205 to determine whether the electrical signal data 262 of the occupant within the vehicle 110 is similar to at least one of the one or more user profiles stored in the user profile data 270. In particular, the identity confirmation logic 248 of the driver support system 100 determines whether the occupant has a registered user profile by initially aligning the corresponding electrical signal at the predetermined frequency of the electrical signal data 262 to an identical electrical signal at the same predetermined frequency from each of the one or more user profiles in the user profile data 270. In this instance, by aligning the electrical signal data 262 of the occupant to the electrical signal data included in each of the one or more user profiles of the user profile data 270, the surrounding electrical signal data 262 of the occupant relative to the signal at the predetermined frequency may be compared to the surrounding electrical signal data in each of the one or more user profiles of the user profile data 270.

At step 512, upon determining that an identity of the occupant within the vehicle 110 matches at least one of the user profiles stored within the user profile data 270 based on the comparative analysis of the brainwave signals of the occupant to the registered brainwave signals stored in the one or more user profiles of the user profile data 270 as described above, the identity confirmation logic 248 causes the processing device 205 to permit a start-function of the vehicle 110. Additionally, at step 514, the identity confirmation logic 248 causes the processing device 205 to upload preprogrammed vehicle system settings to be applied to the various components of the vehicle 110. For example, each of the one or more user profiles stored in the user profile data 270 may include user-specified preferences and settings for the user interface hardware 215 of the vehicle 110, the vehicle systems control hardware 230, and the like. The preprogrammed settings and/or preferences may be autonomously uploaded once an identity of the occupant is confirmed and the user profile is applied to promote a convenience and comfort for the occupant in operating the vehicle 110.

Still referring to FIG. 9, alternatively, at step 516, in response to determining at step 510 that an identity of the occupant within the vehicle 110 does not match at least one of the user profiles stored within the user profile data 270 based on the comparative analysis of the brainwave signals of the occupant to the registered brainwave signals stored in the one or more user profiles of the user profile data 270, the identity confirmation logic 248 causes the processing device 205 to inhibit, prevent, and/or lock a start-function of the vehicle 110. In this instance, the occupant within the vehicle 110 may not be identified as a registered user of the vehicle 110 such that the driver support system 100 determines that the occupant is not authorized to operate the vehicle 110.

Figure 10:
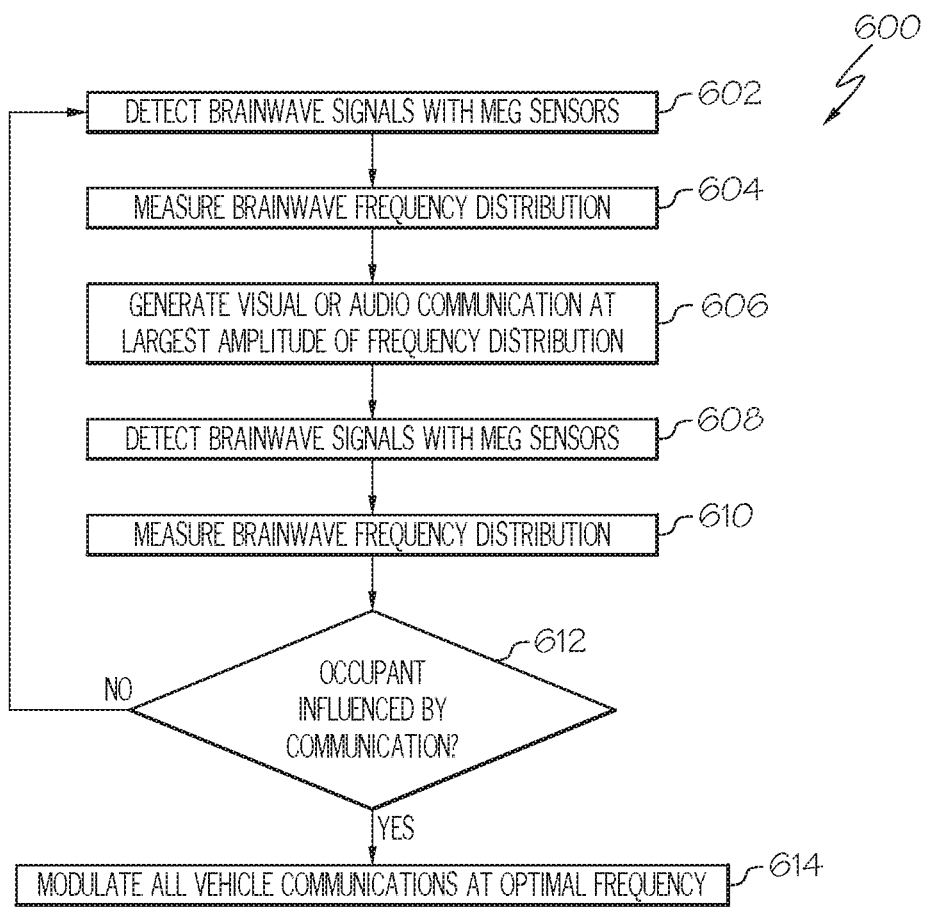
FIG. 10 depicts a flow diagram of yet another illustrative method of generating communications within a vehicle at an optimal frequency with the driving support system of FIG. 1 according to one or more embodiments shown and described herein.

Referring now to FIG. 10, an illustrative method of enhanced brain entrainment is depicted where communications may be transmitted to an occupant of the vehicle 110 at optimal frequencies, generally designated 600, according to some embodiments. The various steps described with respect to FIG. 10 are merely illustrative, and additional, fewer, or alternative steps are contemplated without departing from the scope of the present disclosure. It should be understood that in some embodiments, the driver support system 100 is not configured to autonomously initiate a driver support control or measure (i.e., a communication at an optimal frequency) to the vehicle 110. In addition, the steps described with respect to FIG. 10 are generally completed when the vehicle 110 is in active operation.

As one non-limiting example, as the vehicle 110 is being actively operated, various components of the user interface hardware 215, the vehicle systems control hardware 230, and/or the like may require communicating information to an occupant of the vehicle 110. For instance, communications of the display output hardware or audio output hardware of the user interface hardware 215, or one or more components of the vehicle systems control hardware 230 may generate an alert or notification for transmission to an occupant of the vehicle 110 via a visual or audible communication. Such communications may be presented to an occupant at an optimal frequency, based on the brainwave signals of the occupant at an instance when the communication is to be transmitted, to effectively transmit the communication. In other words, manipulating a communication to an occupant of the vehicle at a particular modulation frequency may improve an effective receipt of the communication by the occupant. Synchronizing a modulation of a communication with a frequency of a brain of the occupant may promote a transmission and recognition of information by the occupant.

As the occupant actively operates the vehicle 110 the occupant may be positioned on the seat 112, 122 with a head of the occupant located relatively proximate to the headrest 114, 124 of the seat 112, 122. The occupant may experience neural activity within a central nervous system of the occupant's body, and in particular, within a head of the occupant where the brain is located. With the headrest 114, 124 of the seat 112, 122 including one or more sensors 250 therein (FIGS. 3-5), and in particular, at least one neuroimaging sensor 252 (e.g., MEG sensor), the brainwave signals of the occupant may be detected by the driver support system 100 prior to transmitting a communication to the occupant via the driver support system 100.

Still referring to FIG. 10, at step 602, the one or more programming instructions included in the memory component 240, such as the brainwave detection logic 242, when executed by the processing device 205, causes the processing device 205 to initiate the one or more sensors 250 capable of sensing brainwave signals from an area adjacent to the headrest 114, 124 of the seat 112, 122. In particular, the neuroimaging sensor 252 of the driver support system 100 actively detects any brainwave signals within a detection field of the neuroimaging sensor 252. The brainwave detection logic 242, when executed by the processing device 205, causes the processing device 205 to record the brainwave signals and store the corresponding electrical signal data 262 in the data storage device 225 of the driver support system 100.

At step 604, the driving support logic 247, when executed by the processing device 205, causes the processing device 205 to measure a brainwave frequency distribution from the electrical signal data 262 detected to estimate a minimum amplitude and a maximum amplitude of the frequency distribution. At step 606, the driving support logic 247 when executed by the processing device 205 causes a communication to be transmitted to an occupant of the vehicle 110 at a maximum amplitude frequency of the brainwave frequency distribution. It should be understood that the communication may be in the form of a visual output via the display output hardware of the user interface hardware 215 (e.g., visual indicators), an audible output via the audible output hardware of the user interface hardware 215 (e.g., automated voice message), and the like. For example, if a visual indicator is generated along the HUD display of the front windshield 115 of the vehicle 110, the visual indicator will be displayed thereon at the maximum amplitude frequency.

Referring still to FIG. 10, at step 608, the brainwave detection logic 242, when executed by the processing device 205, causes the processing device 205 to initiate the one or more neuroimaging sensors 252 of the driver support system 100 to detect the brainwave signals generated in response to the communication at the maximum amplitude frequency. The brainwave detection logic 242, when executed by the processing device 205, causes the processing device 205 to record the brainwave signals and store the corresponding electrical signal data 262 in the data storage device 225 of the driver support system 100.

At step 610, the optimal frequency communication logic 249, when executed by the processing device 205, causes the processing device 205 to measure a subsequent brainwave frequency distribution from the electrical signal data 262 detected to estimate a subsequent minimum amplitude and a subsequent maximum amplitude of the frequency distribution. At step 612, the optimal frequency communication logic 249, when executed by the processing device 205, causes the processing device 205 to determine if the subsequent amplitudes of the frequency distribution were influenced (i.e., enhanced) relative to the original amplitudes of the initial frequency distribution. In other words, the optimal frequency communication logic 249 executed by the processing device 205 determines an optimal frequency for transmitting future communications to the occupant based on analyzing the subsequent brainwave frequency distribution generated by the communication at the maximum amplitude frequency and determining whether the brainwave signals experienced by the occupant were heightened as a result.

Still referring to FIG. 10, at step 614, the optimal frequency communication logic 249, when executed by the processing device 205, causes the processing device 205 to, upon determining that the brainwave signals detected by the neuroimaging sensors 252 were enhanced, and in particular the amplitudes of the subsequent brainwave frequency distribution, modulate all further communications from the driver support system 100 and/or the components of the vehicle 110 to the occupant at the optimal frequency. For example, the processing device 205, when executing the operating logic 241 to transmit an audible communication to an operator of the vehicle 110 via an audible output hardware of the user interface hardware 215 (e.g., speakers), may modulate the audio signal at the optimal frequency. By way of further example, the processing device 205, when executing the operating logic 241 to transmit a visual communication to an operator of the vehicle 110 via a display output hardware of the user interface hardware 215 (e.g., display screen) may module the visual signal at the optimal frequency by pulsing the light producing the visual communication at the optimal frequency. Alternatively, upon determining that the brainwave signals detected by the neuroimaging sensors 252, and in particular the amplitudes of the subsequent brainwave frequency distribution, were not enhanced at step 614, the process 600 returns to step 602 to measure a brainwave frequency distribution of the occupant and estimate the amplitudes again.

In this instance, upon measuring a brainwave frequency distribution from the electrical signal data 262 at step 604 to estimate a minimum amplitude and a maximum amplitude of the frequency distribution, the driving support logic 247 when executed by the processing device 205 causes a communication to be transmitted to an occupant of the vehicle 110 at step 606. The communication transmitted at step 606 is generated at a second-maximum amplitude frequency of the brainwave frequency distribution, rather than a maximum amplitude frequency as previously described above. In other words, the driver support system 100 generates a communication at step 606 that varies relative to the initial communication generated at step 606 by transmitting the subsequent communication at a frequency different than the maximum amplitude frequency initially transmitted to the occupant. In this instance, it may be determined whether the adjusted communication provides enhanced perception of the information by the occupant.

In the embodiments described herein, the terms "internal" and "external" are used to describe the relative positioning of various components of the vehicle or otherwise with respect to a passenger cabin of the vehicle. As used herein, the terms "lateral," "longitudinal," "inward," "outward," "distal," "adjacent," "proximal" and "proximate" are used to describe the relative positioning of various components of the assembly.

It should now be understood that the driver support systems described herein may include one or more sensors positioned within a vehicle, such as neuroimaging sensor that detects neurological signals of an occupant of the vehicle and a positioning sensor that detects a position of the occupant relative to the neuroimaging sensor. The driver support systems described herein generally include various non-invasive components that determine a mental state of the occupant based on the neurological signals detected and initiate a vehicle support control measure in response to determining the mental state of the occupant.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A driver support system of a vehicle comprising:
   a neuroimaging sensor that detects neurological signals of an occupant of the vehicle, wherein the neuroimaging sensor is configured to be positioned within the vehicle distally from the occupant such that the neuroimaging sensor is adjacent to the occupant;
   a positioning sensor that detects a position of the occupant relative to the neuroimaging sensor; and
   a processor;
   non-transitory computer-readable medium storing computer-readable instructions that, when executed, causes the processor to:
      generate a brain activity map of the occupant based on the neurological signals detected by the neuroimaging sensor;
      calibrate the brain activity map by reorienting the brain activity map based on the position of the occupant relative to the neuroimaging sensor;
      determine a mental state of the occupant based on the calibrated brain activity map; and
      actuate vehicle support control in response to determining the mental state of the occupant.

2. The driver support system of claim 1, wherein the neuroimaging sensor is a magnetoencephalography sensor embedded within a seat of the vehicle.

3. The driver support system of claim 1, wherein the positioning sensor comprises a pressure sensor that detects a force applied thereto by the occupant or an imaging sensor that captures an image of the occupant within the vehicle.

4. The driver support system of claim 3, wherein the non-transitory computer-readable medium storing computer-readable instructions that, when executed, causes the processor to determine the position of the occupant relative to the vehicle based on the force detected by the pressure sensor or the image captured by the imaging sensor.

5. The driver support system of claim 4, wherein the non-transitory computer-readable medium storing computer-readable instructions thereon causes the processor to, when executed, calibrate the brain activity map by reorienting the brain activity map based on the position of the occupant as determined by the detected force or image.

6. The driver support system of claim 1, wherein the non-transitory computer-readable medium storing computer-readable instructions thereon causes the processor to, when executed, compare the calibrated brain activity map to brain activity pattern data indicative of stored user profiles.

7. The driver support system of claim 1, wherein the non-transitory computer-readable medium storing computer-readable instructions thereon causes the processor to, when executed, generate one or more visual notifications along a front windshield or a mirror of the vehicle at a location corresponding to an object external to the vehicle.

8. The driver support system of claim 7, wherein the one or more visual notifications are displayed at varying predetermined frequencies.

9. The driver support system of claim 8, wherein the non-transitory computer-readable medium storing computer-readable instructions thereon causes the processor to, when executed, determine whether the occupant detects the one or more visual notifications based on identifying the predetermined frequency of the respective visual notification from the neurological signals detected by the neuroimaging sensor.

10. The driver support system of claim 9, wherein the non-transitory computer-readable medium storing computer-readable instructions thereon causes the processor to, when executed, cease the one or more visual notifications along the front windshield or the mirror in response to determining the occupant detects the predetermined frequency of the respective visual notification.

11. A vehicle comprising:
a seat for supporting an occupant received thereon;
a driver support system including at least one neuroimaging sensor and at least one positioning sensor, the neuroimaging sensor detects neurological signals of the occupant and the positioning sensor detects a position of the occupant relative to the neuroimaging sensor, wherein the neuroimaging sensor is configured to be positioned along the seat and adjacent to the occupant received thereon;
a processor;
non-transitory computer-readable medium storing computer-readable instructions thereon that, when executed, causes the processor to:
generate a brain activity map of the occupant based on the neurological signals detected by the neuroimaging sensor;
calibrate the brain activity map based on the position of the occupant relative to the neuroimaging sensor;
determine an emotional state of the occupant based on the calibrated brain activity map; and
initiate control of a vehicle system in response to determining the emotional state of the occupant.

12. The vehicle of claim 11, wherein the vehicle system includes vehicle steering, braking, and accelerating.

13. The vehicle of claim 11, wherein the vehicle system includes an HVAC device of the vehicle.

14. The vehicle of claim 11, wherein vehicle system includes an audio or visual device of the vehicle.

15. The vehicle of claim 11, wherein the at least one positioning sensor includes an imaging sensor that captures images of the occupant received on the seat and a pressure sensor that detects forces of occupant when received on the seat.

16. A method of autonomously supporting driver control of a vehicle, comprising:
generating a visual indicator along a surface of the vehicle within a field of view of a driver at a predetermined frequency, wherein the location of the visual indicator corresponds to a relative location of a target object that is to be identified by the occupant;
detecting a neurological signal of the occupant by a neuroimaging sensor positioned within the vehicle proximate to the occupant;
determining whether the occupant identified the visual indicator based on the neurological signal detected by the neuroimaging sensor; and
initiating control of a driver support system in response to determining that the occupant identified the visual indicator.

17. The method of claim 16, wherein the surface includes a heads-up display, a rearview mirror or a side mirror.

18. The method of claim 17, wherein the driver support system includes the visual indicator such that the method further comprises:
ceasing the visual indicator along the surface in response to determining the occupant identified the visual indicator; and
repeating the visual indicator along the surface in response to determining the occupant did not identify the visual indicator.

19. The method of claim 16, wherein the driver support system includes a vehicle start-function, such that the method further comprises:
generating a second visual indicator along the surface of the vehicle at a predetermined frequency;
generating a brain activity map of the occupant based on the neurological signals detected by the neuroimaging sensor in response to determining the occupant identified the second visual indicator;
determining an identity of the occupant by comparing the brain activity map to brain activity pattern data indicative of stored-user profiles; and
determining whether the identity of the occupant corresponds to at least one stored-user profile.

20. The method of claim 16, wherein the driver support system includes a visual or audio communication device such that the method further comprises:
determining an optimal communication frequency based on the neurological signals detected by the neuroimaging sensor when the occupant perceives the visual or audio communication; and
generating a communication via the visual or audio communication device at the optimal frequency.

* * * * *